United States Patent [19]

Datta et al.

[11] Patent Number: 4,892,534
[45] Date of Patent: Jan. 9, 1990

[54] NONWOVEN WEB USEFUL AS A BODYSIDE LINER FOR AN ABSORPTION ARTICLE

[75] Inventors: Paul J. Datta; Gary C. Anderson, both of Appleton, Wis.

[73] Assignee: Kimberly-Clark Corporation, Neenah, Wis.

[21] Appl. No.: 292,600

[22] Filed: Dec. 30, 1988

[51] Int. Cl.4 ............................................... A61F 13/16
[52] U.S. Cl. .................................... 604/370; 428/224; 428/227; 428/284; 428/286; 428/296; 428/297; 428/298; 428/299; 428/397; 428/913
[58] Field of Search ............... 428/224, 227, 284, 286, 428/296, 297, 298, 299, 397, 913; 604/358, 370

[56] References Cited

U.S. PATENT DOCUMENTS

| | | | |
|---|---|---|---|
| 3,886,942 | 6/1975 | Bernardin et al. | 128/290 |
| 4,077,410 | 3/1968 | Butterworth | 128/287 |
| 4,166,877 | 9/1979 | Brandon | 428/227 |
| 4,333,979 | 6/1982 | Sciaraffa et al. | 428/179 |
| 4,341,213 | 7/1982 | Cohen | 128/284 |
| 4,405,297 | 9/1983 | Appel et al. | 425/72 |
| 4,426,420 | 4/1984 | Likhyani | 428/299 |
| 4,472,328 | 9/1984 | Sugimoto | 264/41 |
| 4,483,897 | 11/1984 | Fujimura | 428/288 |
| 4,519,799 | 5/1985 | Sakurai et al. | 604/366 |

FOREIGN PATENT DOCUMENTS

| | | |
|---|---|---|
| 0039974 | 5/1981 | European Pat. Off. . |
| 0140560 | 9/1984 | European Pat. Off. . |
| 0164740 | 6/1985 | European Pat. Off. . |
| 0172420 | 7/1985 | European Pat. Off. . |

Primary Examiner—James J. Bell
Attorney, Agent, or Firm—Thomas J. Connelly

[57] ABSTRACT

A liquid-permeable, nonwoven web is disclosed which is useful as a bodyside liner for an absorption article, particularly baby diapers, incontinent garments and feminine care products. The nonwoven web contains at least 3 layers of thermoplastic filaments which are bonded together. The filaments have a denier of between about 3 to 15. The web has a basis weight of between about 0.5 to 1.0 ounces per square yard and a length of fiber per unit volume of between about 100 to 400 meters per cubic centimeter. A web constructed according to the above description provides good masking properties for body exudate, especially menstrual fluid, which comes in contact with it. The web also permits a rapid passage of human exudate therethrough into an adjacent absorbent where it can be retained.

22 Claims, 4 Drawing Sheets

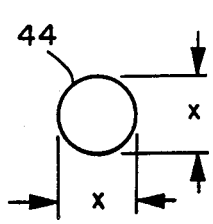
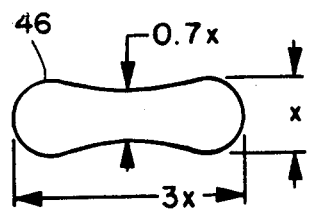
FIG. 7  FIG. 8
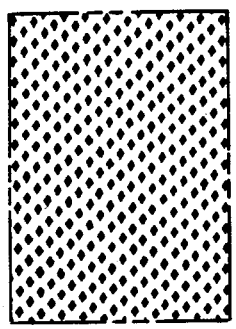
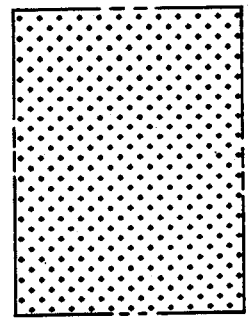
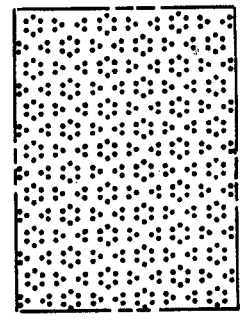
FIG. 9  FIG. 10  FIG. 11

NONWOVEN WEB USEFUL AS A BODYSIDE LINER FOR AN ABSORPTION ARTICLE

FIELD OF THE INVENTION

This invention relates to a liquid-permeable, nonwoven web useful as a bodyside liner for an absorption article, particularly sanitary napkins.

BACKGROUND OF THE INVENTION

The formation of absorbent articles for use as diapers, incontinent garments, feminine care products, etc., has generally involved the combination of a liquid-impermeable backing material, a liquid-permeable bodyside liner and an absorbent positioned therebetween. Body exudate, particularly menstrual fluid in the case of feminine napkins, which impinges upon the absorbent article is intended to pass through the liquid-permeable liner and be absorbed by the absorbent below. The liquid-impermeable backing material serves to prevent the exudate from passing through the article and staining the clothes of the wearer. It has been found that consumers in general do not prefer to look at the exudate absorbed by the article. Therefore, there is a desire to provide absorbent articles, particularly sanitary napkins, which contain a liquid-permeable liner that will mask the body exudate which comes in contact with it. The liquid-permeable liner must also exhibit the ability to rapidly transport body exudate therethrough.

Several alternatives have been proposed to make the liquid-permeable liner better at masking body exudate which comes in contact with it. In U.S. Pat. No. 4,333,979 issued to Sciaraffa et al., a spunbonded web is taught containing up to 5 percent of inorganic pigments so as to provide the liner with an opaque coloration. In U.S. Ser. No. 07/036,936 filed Apr. 10, 1987 by Datta et al. and assigned to Kimberly-Clark Corporation, a liquid-permeable nonwoven web is disclosed which is useful as a cover material for feminine pads. The web has a denier greater than 3 and has at least 1 percent of a colorant added to assist in masking body exudate. The web has an average pore size of about 15,000 to 100,000 square microns, an open area of about 25 to 50 percent and a weight of about 0.28 to 0.5 ounces per square yard. U.S. Pat. Nos. 4,341,213; 4,472,328; 4,483,897 and European Patents Nos. 0 140 560 and 0 172 420 all teach variations of adding pigments to the cover material.

A second alternative is to use a nonwoven fabric formed from a web of thermoplastic fibers having a plurality of apertures formed therein. The apertures allow fluid to pass through the liner while the nonapertured areas provide a masking effect. The liner can also be embossed to provide a similar benefit, such as is taught in European Patent No. 0 164 740. A third alternative is to make the liner from a web which is intermittently and autogenously bonded at discrete bond areas. The use of unfinished polyolefin or polyester fibers can provide such a web texture as is disclosed in U.S. Pat. No. 3,886,942. Two variations of spunbonded facing webs having a denier below 3, are taught in U.S. Pat. Nos. 4,077,410 and 4,519,799.

A fourth alternative is taught in European Patent No. 0 039 974 wherein a film topsheet containing a plurality of apertures overlays an intermediate layer having a multiplicity of tapered capillaries. The tapered capillaries are designed to draw fluid through the topsheet and into an absorbent below. One disadvantage of this design is that it requires a separate intermediate layer, which adds cost to the finished product.

In view of the above-identified prior art, there still exists a need to produce a liner which has its own unique properties such that it will allow body exudate, particularly menstrual fluid, to pass through it while masking the body exudate which is absorbed by the absorbent below. Now a nonwoven web has been invented which can accomplish the above.

SUMMARY OF THE INVENTION

Briefly, the present invention relates to a liquid-permeable, nonwoven web useful as a bodyside liner for an absorption article such as baby diapers, incontinent garments, feminine care products, panty liners, etc. The nonwoven web contains at least three layers of thermoplastic filaments which are randomly bonded together. The filaments have a denier of between about 3 to 15, while the web has a basis weight of between about 0.5 to 1.0 ounces per square yard and a length of fiber per unit volume of between about 100 to 400 meters per cubic centimeter.

The general object of this invention is to provide a nonwoven web useful as a bodyside liner for an absorption article. A more specific object of this invention is to provide a nonwoven web with sufficient open area to allow menstrual fluid to pass through while containing sufficient masking properties to mask the menstrual fluid absorbed by the absorbent below.

Another object of this invention is to provide a liquid-permeable, nonwoven web useful as the bodyside liner for a feminine napkin.

Still another object of this invention is to provide an inexpensive nonwoven liner for a feminine napkin which is relatively simple to construct and economical to form into a liner material.

Still further, an object of this invention is to provide a liquid-permeable, nonwoven web which permits fast absorbency of human exudate while providing a dry surface to the wearer and good hiding properties for the human exudate which has passed through the liner.

Other objects and advantages of the present invention will become more apparent to those skilled in the art in view of the following description in the accompanying drawings.

BRIEF DESCRIPTION OF THE DRAWINGS

FIG. 7 is a cross-sectional view of a round fiber utilized in forming the nonwoven web.

FIG. 8 is a cross-sectional view of a bilobal fiber utilized in forming the nonwoven web.

FIG. 9 is an illustration of a nonwoven web having a bond area of about 20 to 30 percent with the bond area being represented by a diamond pattern.

FIG. 10 is an illustration of a nonwoven web having a bond area of about 12 to 20 percent with the bond areas being represented by a diamond pattern.

FIG. 11 is an illustration of a nonwoven web having a bond area of about 20 to 32 percent with the bond areas having a round hexagonal triangular pattern.

DETAILED DESCRIPTION OF THE PREFERRED EMBODIMENTS

Figure 1:
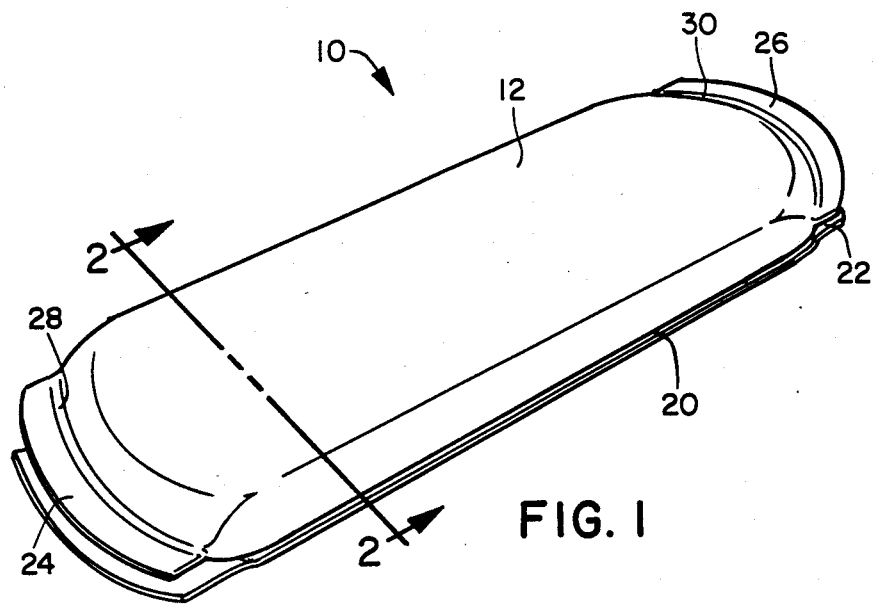
FIG. 1 is a perspective view of a feminine napkin.
Figure 2:
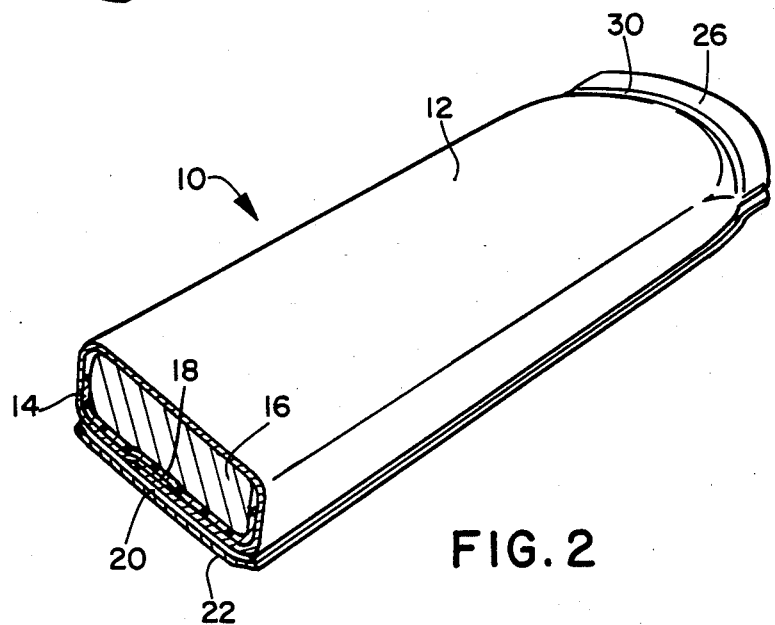
FIG. 2 is a sectional view of the feminine napkin shown in FIG. 1 taken along line 2—2.
Figure 3:
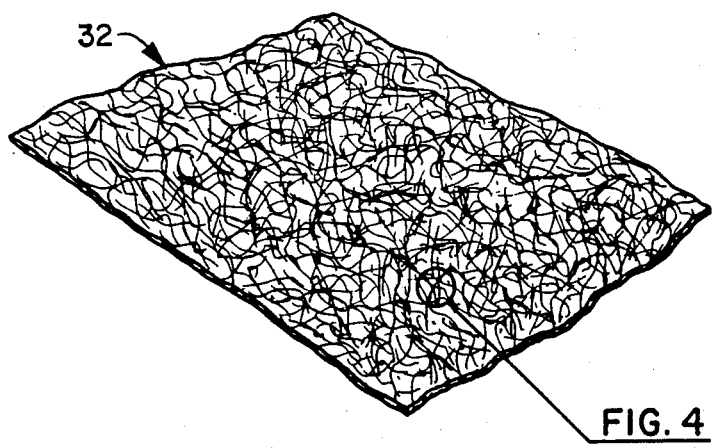
FIG. 3 is an enlarged view of a portion of the bodyside liner shown in FIG. 2.
Figure 4:
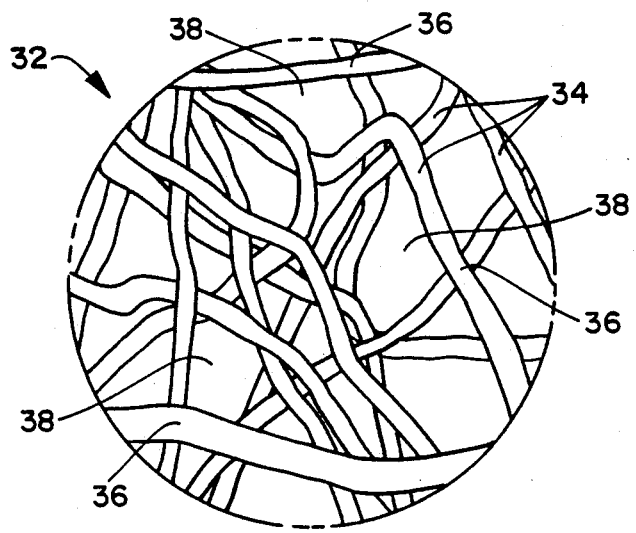
FIG. 4 is a magnified view of the circled portion of the liner shown in FIG. 3 at a magnification of 30X and shows the open areas present between the layered filaments.

Referring to FIGS. 1 and 2, an absorbent article in the shape of a feminine napkin 10 is shown constructed of a liquid-permeable liner 12 and a liquid impermeable baffle 14 which cooperate to enclose an absorbent 16. The liner 12 completely surrounds both the baffle 14 and the absorbent 16 and is overlapped upon itself at 18 on a surface which is opposite from the bodyside surface which contacts the body of a user. The sanitary napkin 10 also contains a garment adhesive strip 20 which is covered by a releasable peel strip 22. Before use, the consumer removes the peel strip 22 and attaches the napkin 10, by means of the adhesive strip 20, to an inside surface of an undergarment.

The sanitary napkin 10 also contains ends 24 and 26 which are arcuate in shape and contain seal lines 28 and 30, respectively. The seal lines 28 and 30 bond the baffle 14 to the liner 12 so as to form a stable product. It should be noted that although the absorbent article is described as a sanitary napkin 10, it is possible that the liquid-permeable, nonwoven web could be utilized in baby diapers, incontinent garments, panty liners, bed sheets, face masks, operating gowns, drapes, bandages, wound dressings, etc. The web 12 could also be used as an agricultural fabric to filter sunlight or to provide a mulch.

Referring to FIGS. 3-6, the liner 12 is comprised of a nonwoven web 32 which has at least 3 layers and preferably between 3 and 8 layers of thermoplastic filaments 34. The web 32 is a spunbonded product which can be made from copolymers of polypropylene and polyethylene, linear low-density polyethylene, other polyolefins or polyesters. A preferred material is melt spinnable polypropylene, particularly fiber-grade, high-isotactic polypropylene. Polypropylene is preferred for it is low in cost, readily spinnable and provides a good feel to the fabric formed from the filaments. The thickness of the web 32 can vary but preferably it is between about 3 to 8 mils. The thermoplastic filaments 34 are laid down in a random fashion, one layer on top of another, and the filaments 34 are bonded to adjacent filaments at their intersections 36 as is shown in the magnified view of FIG. 4. The web 32 also has a plurality of open areas 38 formed between the filaments 34. The open areas 38 allow body exudate, particularly menstrual fluid, to be rapidly absorbed by the web 32 and pass through into the adjacent absorbent 16 where it is retained. The filaments 34 have a diameter of about 25 to 35 microns and a denier of between about 3 to 15, preferably between about 4 to 10 and most preferably between about 4 to 6. The diameter and denier are larger and coarser, respectively, than normally used for liner material, especially liners for feminine care products, baby diapers and incontinence garments. However, the larger diameter still provides good strength, a soft feel and good hiding ability to the overall web 32. The liner 12 may be treated with a surfactant, if desired, to provide the spunbonded filaments 34 with the ability to absorb liquids.

Denier is by definition: "the mass in grams of a fiber 9,000 meters long". Denier can be calculated using the following formula:

$$\text{Denier} = \frac{\text{Fiber mass (g)}}{\text{Fiber length (m)}} \times 9{,}000 \text{ m}$$

$$\frac{\text{Fiber mass}}{\text{Fiber length}} = \frac{\text{Fiber diameter}^2}{2} \times \text{Fiber density}$$

The number of fiber layers within a web can nominally be calculated using the following formula:

Number of Fiber Layers = Fabric thickness/Fiber diameter

Figure 5:
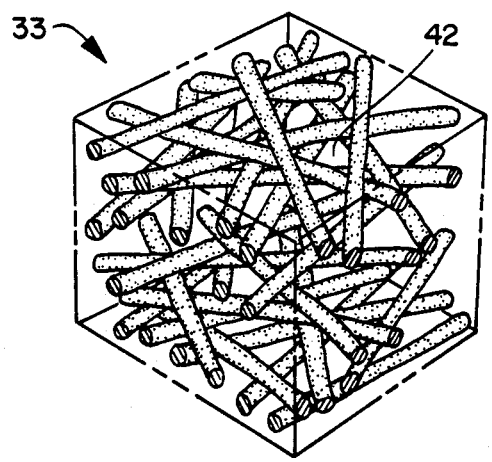
FIG. 5 is an enlarged perspective view of a cubic volume of prior art liner material showing length of fibers per unit volume in meters per cubic centimeters ($m/cm^3$), wherein the fibers have a diameter of less than 20 microns and a denier of less than 3. The web contains more than 8 layers and the length of fiber per unit volume is greater than 500 $m/cm^3$. Such a material is taught in U.S. Pat. No. 3,886,942.
Figure 6:
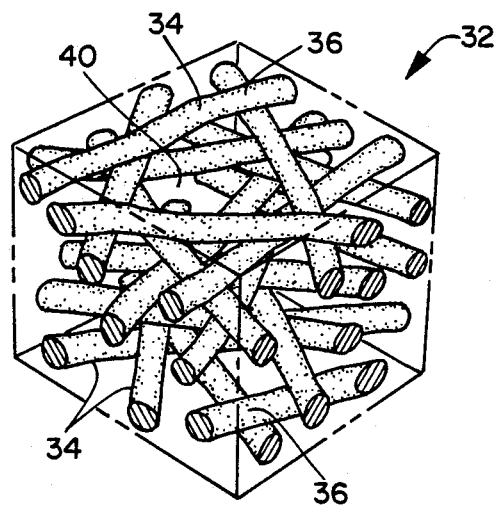
FIG. 6 is an enlarged perspective view of a cubic volume of liner material of this invention showing length of fiber per unit volume ($m/cm^3$) wherein the fibers have a diameter of from about 25 to 35 microns and a denier of between 3 to 15. The web contains from 3 to 8 layers and the length of fiber per unit volume is between about 100 and 400 m/cm$^3$.

The web 32 has a basis weight of between about 0.5 to 1.0 ounces per square yard, preferably between about 0.7 to 1.0 ounces per square yard and most preferably between about 0.7 to 0.8 ounces per square yard. This is again much higher than normally used for liner materials for feminine care products or baby diapers. Basis weight can be measured using known scientific procedures which are known to those skilled in the art. The web 32 also contains a length of fiber per unit volume of between about 100 to 400 meters per cubic centimeter (m/cm$^3$), preferably between about 150 to 350 m/cm$^3$. By reducing the number of layers in the web 32 increasing the denier to between about 3 to 15 and using a heavier basis weight, one can construct a web which contains large passageways 40. The passageways 40 extend downward through the thickness of the web 32 and are larger than those formed by known procedures. In prior art webs, more than 15 layers are present, the filaments have a denier of less than 3 and a much lower basis weight is used, as is depicted in FIG. 5. One can see that a passageways 42 formed through prior art webs 33 contain a much smaller surface area than the passageways 40 formed in the present nonwoven web 32.

The length of fiber per unit volume (i.e., one cubic centimeter), can be calculated using the following formula:

$$\frac{\text{Fiber length (m)}}{\text{Volume of fabric (cm}^3\text{)}} = \frac{\text{Basis Weight of fabric (g/cm}^2\text{)}}{\text{Fabric thickness (cm)}} \times \frac{9{,}000 \text{ (m)}}{\text{Denier (g)}}$$

Experimental data relating to the present invention is contained in Table 1, along with comparative data for prior art nonwoven webs referred to as Lurgi.

TABLE 1

| Sample No. | Nonwoven Web | No. of Fiber Layers | Cross-Sectional Shape of Fiber | Fiber Denier | Basis Weight of Web | | Length of Fibers per Unit Volume m/cm$^3$ | Density of an Individual Fiber gm/cm$^3$ | Fiber Diameter microns (10–6 m) | Thickness of Web | |
|---|---|---|---|---|---|---|---|---|---|---|---|
| | | | | g | oz/yd$^2$ | g/m$^2$ | | | | mils. (10–3 in.) | microns (10–6 m) |
| 1 | LDS* | 3.18 | round | 4.30 | 0.40 | 13.56 | 346 | 0.929 | 25.70 | 3.22 | 81.8 |
| 2 | LDS* | 3.29 | round | 6.34 | 0.40 | 13.56 | 188 | 0.929 | 31.08 | 4.03 | 102.4 |
| 3 | LDS* | 3.62 | round | 6.34 | 0.45 | 15.25 | 192 | 0.929 | 31.08 | 4.43 | 112.5 |
| 4 | LDS* | 4.02 | round | 6.34 | 0.50 | 16.95 | 193 | 0.929 | 31.08 | 4.92 | 125.0 |
| 5 | LDS* | 5.08 | round | 6.60 | 0.60 | 20.34 | 170 | 0.929 | 32.10 | 5.36 | 163.2 |
| 6 | LDS* | 5.30 | round | 6.34 | 0.60 | 20.34 | 175 | 0.929 | 31.08 | 6.48 | 164.6 |
| 7 | LDS* | 6.22 | round | 5.24 | 0.80 | 27.12 | 223 | 0.929 | 28.25 | 6.92 | 175.8 |
| 8 | LDS* | 7.91 | round | 4.30 | 1.00 | 33.90 | 348 | 0.929 | 25.70 | 8.00 | 203.4 |
| PRIOR ART | | | | | | | | | | | |
| 9 | LURGI** | 4.85 | round | 1.99 | 0.40 | 13.56 | 716 | 0.907 | 17.66 | 3.37 | 85.6 |
| 10 | LURGI** | 9.32 | round | 2.33 | 0.70 | 23.73 | 667 | 0.907 | 19.07 | 5.42 | 137.7 |

*Nonwoven web formed by a linear drawn spunbonded process as taught in U.S. Pat. No. 4,405,297.
**Nonwoven web formed by a spunbonded process as taught in U.S. Pat. No. 3,886,942.

The nonwoven web 32 is formed by a linear drawn spunbonded process as taught in U.S. Pat. No. 4,405,297 which is assigned to the present assignee and incorporated by reference and made a part hereof. The prior art material is formed by a spunbonded process referred to a Lurgi and is taught in U.S. Pat. No. 3,886,942 which is also assigned to the present assignee. The U.S. Pat. No. 3,886,942 is also incorporated by reference and made a part hereof. In Table 1, one can see that the sample nonwoven webs numbered 1 to 8, which encompass the present invention, contain anywhere from 3 to 8 spunbonded polymer fiber layers. The sample fibers had a round cross-sectional shape 44, see FIG. 7, and a constant radius. It should be noted that bilobal fibers 46, as shown in FIG. 8, which have an hourglass shape, can also be used. The value for x in either the round 44 or bilobal fibers 46 should be between about 25 to 35 microns. It should also be noted that other cross-sectional shapes for fibers may work as well.

Table 1 further shows the "Fiber Denier" to be at least twice and preferably three times larger than the denier of prior art filaments. The "Length of Fiber per Unit Volume" (m/cm$^3$) is much lower than that of prior art webs wherein finer filaments and more compacted layers are utilized. This corresponds with fiber diameter which is much higher in the present nonwoven web 32, i.e., between about 25 to 35 microns, whereas prior art fibers normally have a diameter of below 20 microns. One should also notice that the thickness of the present nonwoven web 32 is in the same range as the thickness of the prior art web, although the number of fiber layers has been reduced. This is as would be expected for it allows the passageways 40 to be larger in surface area and therefore allow a much faster or quicker passage of menstrual fluid and body exudate through the liner 12. Lastly, Table 1 lists the "Density of Individual Fibers" in grams per cubic centimeter (g/cm$^3$). The density of an individual fiber can be calculated using the following formula:

$$\text{Density of an individual fiber} = \frac{\text{mass}}{\text{volume}}$$

$$\text{Density of an individual fiber} = \frac{\text{mass of colorant} + \text{mass of filament material}}{\text{volume of the mixture}}$$

A colorant, such as titanium dioxide or calcium carbonate, can be added to the filament material to produce a white color. Titanium dioxide is preferred because it is inert, heat stable, very white in color and is easy to process. Preferably, sufficient colorant is added to the nonwoven web 32 to provide opacity sufficient to mask any body exudate absorbed by the product. When the colorant is titanium dioxide, it is preferable to add about 1 to 6 percent by weight of the finished liner. A more preferred range is between about 3 to 4 percent by weight.

The following example is based on the use of a small percentage of a colorant:

LDS=96% polypropylene (PP) and 4% titanium dioxide (TiO$_2$) by measured weight.

Lurgi=99% polypropylene (PP) and 1% titanium dioxide (TiO$_2$) by measured weight.

NOTE: LDS and Lurgi are processes described in U.S. patents listed at the bottom of Table 1.

The LDS fabric has a higher fiber density due to a higher loading of titanium dioxide.

If the density of PP=0.90 g/cm$^3$, and
if the density of TiO$_2$=4.20 g/cm$^3$.

An example of a density calculation for a 100 gram sample of Lurgi having 99% polypropylene and 1% titanium dioxide:

$$\text{Volume of TiO}_2 = \frac{\text{Mass of TiO}_2}{\text{Density of TiO}_2}$$

$$= \frac{1 \text{ gram of TiO}_2}{4.20 \text{ g/cm}^3} = 0.2381 \text{ cm}^3;$$

$$\text{Volume of PP} = \frac{99 \text{ grams of PP}}{0.90 \text{ g/cm}^3} = 110 \text{ cm};$$

$$\text{Density of Lurgi} = \frac{\text{Mass}}{\text{Volume}}$$

$$= \frac{1 \text{ gram of TiO}_2 + 99 \text{ grams of PP}}{0.2381 \text{ cm}^3 + 110 \text{ cm}^3} =$$

$$0.907 \text{ g/cm}^3$$

Referring to FIGS. 9–11, three examples of liquid-permeable, nonwoven webs are shown where the bond areas of the filaments varies as a percentage of the total surface area of the web. In FIG. 9, a diamond pattern is shown having a bond area of between 20 and 30 percent. In FIG. 10, a diamond pattern is shown having a bond area of between 12 and 20 percent. Lastly, in FIG. 11, a round hexagonal triangular pattern is shown having a bond area of between 20 and 32 percent. The bond area should be between about 10 to 35 percent of the total surface area of the web and preferably, about 10 to 20 percent. It should be noted that when the bond area is increased above 35 percent, the surface area of the passageways formed through the web will usually become smaller and this reduces the ability of the web to pass menstrual fluid or body exudate through it in a rapid fashion.

The relatively heavier denier spunbonded filaments 34 utilized in the nonwoven web 32 are easier to extrude from a manufacturing standpoint than are finer filaments. The heavier denier filaments produce a web having a lighter weight, which lowers the cost of the web since less polymer is needed. The relatively large passageways 40 formed through the web 32 allow clots of menstrual fluid to pass through, thereby presenting a cleaner surface to the ultimate customer, furthermore, since the body exudate is allowed to rapidly pass through the liner 12 into the absorbent 16, the liner 12 looks and feels cleaner to the user.

It should also be mentioned that since the liner 12 is formed from heavier denier filaments having bond areas of between about 10 to 35 percent, that the increase size of the passageways 40 eliminate the need for additional perforating or stretching steps or the need to form apertures therethrough. The liner 12 is soft to the touch and provides good masking properties of the absorbed material. This, coupled with the addition of a colorant, presents a very white and clean look. In the spunbonded process, the filaments 34 are extruded as a continuous polymer string onto a moving substrate. The filaments 34 are somewhat molten when laid down on the substrate and tend to adhere to one another at their intersections 36. This creates the bond areas formed between the filaments 34. It is also possible to increase the inner fiber bonding structure by passing the web through heated calender rolls or subjecting it to heated air to aid in fusion between the filaments 34. If desired, a binder material can be added to the filaments 34 to assist in their bonding.

Experimental data has indicated that the masking ability or hiding power of the present nonwoven web 32 is substantially superior to conventional spunbonded materials utilized in baby diapers and feminine care products. The present liner 12 exhibits an improvement of from 2 to 20 times the masking ability of conventional spunbonded materials. This advantage is obtained without decreasing the absorption rate of body exudate which can be transferred through the liner.

While the invention has been described in conjunction with a specific embodiment, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. A nonwoven web useful as a bodyside liner for an absorption article comprising at least 3 layers of filaments bonded together, said filaments having a denier of between about 3 to 15, said web having a basis weight of between about 0.5 to 1.0 ounces per square yard and a length of fiber per unit volume of between about 100 to 400 meters per cubic centimeter.

2. The nonwoven web of claim 1 wherein said filaments have a round cross-section and are formed from spunbonded polymer fibers.

3. The nonwoven web of claim 1 wherein said filaments have a bilobal cross-sectional configuration and are formed from spunbonded polymer fibers.

4. The nonwoven web of claim 1 wherein said filaments have a denier of between about 4 to 10.

5. The nonwoven web of claim 4 wherein said filaments have a denier of between about 4 to 6.

6. The nonwoven web of claim 1 wherein said filaments have a diameter of between about 25 to 35 microns.

7. The nonwoven web of claim 1 wherein said web has a basis weight of between about 0.7 to 0.8 ounces per square yard.

8. The nonwoven web of claim 1 wherein said web contains about 1 to 6 percent by weight of titanium dioxide.

9. The nonwoven web of claim 1 wherein said filaments are polypropylene.

10. A fluid permeable, nonwoven web useful as a bodyside liner for a feminine pad comprising 3 to 8 layers of thermoplastic filaments bonded together, said filaments having a denier of between about 4 to 10, web having a basis weight of between about 0.7 to 1.0 ounces per square yard and a density of between about 150 to 350 meters per cubic centimeter.

11. The nonwoven web of claim 10 wherein said thermoplastic filaments are bonded together and the area of bonding represents approximately 10 to 35 percent of the total surface area of said web.

12. The nonwoven web of claim 11 wherein said area of bonding represents approximately 10 to 20 percent of the total surface area of said web.

13. The nonwoven web of claim 10 wherein said thermoplastic filaments are polypropylene.

14. The nonwoven web of claim 10 wherein said thermoplastic filaments have a denier of between about 4 to 6.

15. A fluid permeable, nonwoven web useful as a bodyside liner for a feminine pad comprising 3 to 7 layers of filaments bonded together, said filaments having a denier of between about 4 to 10, said web having a basis weight of between about 0.7 to 0.8 ounces per square yard, a length of fiber per unit volume of between about 150 to 350 meters per cubic centimeter and containing about 1 to 6 percent by weight of titanium dioxide.

16. The nonwoven web of claim 15 wherein said filaments have a denier of between about 4 to 6.

17. The nonwoven web of claim 15 wherein said filaments are polypropylene.

18. The nonwoven web of claim 15 wherein said filaments are randomly arranged in layers and the area of bonding represents approximately 20 to 30 percent of the total surface area of said web.

19. The nonwoven web of claim 15 wherein said filaments have a diameter of between about 25 to 35 microns.

20. A fluid permeable, nonwoven web useful as a bodyside liner for an absorption article comprising 3 to 8 layers of thermoplastic filaments bonded together, said filaments having a denier of between about 3 to 15, said web having a basis weight of between about 0.5 to 1.0 ounces per square yard and a length of fiber per unit volume of between about 100 to 400 meters per cubic centimeter.

21. The nonwoven web of claim 20 wherein said thermoplastic filaments have a diameter of between about 25 to 35 microns.

22. The nonwoven web of claim 20 wherein said web has a thickness of between about 3 to 8 mils.

* * * * *